United States Patent [19]

Pastor et al.

[11] Patent Number: 5,266,726
[45] Date of Patent: Nov. 30, 1993

[54] STERICALLY HINDERED OXIME COLOR IMPROVERS FOR POLYOLEFIN PROCESSING

[75] Inventors: Stephen D. Pastor, Danbury, Conn.; Paul A. Odorisio, Edgewater, N.J.

[73] Assignee: Ciba-Geigy Corporation, Ardsley, N.Y.

[21] Appl. No.: 880,456

[22] Filed: May 8, 1992

Related U.S. Application Data

[62] Division of Ser. No. 601,148, Oct. 22, 1990, Pat. No. 5,134,183.

[51] Int. Cl.$^5$ .................. C07C 251/38; C08K 5/33
[52] U.S. Cl. .................. 564/268; 524/186; 524/236; 564/253; 564/265; 564/266; 564/267
[58] Field of Search .............. 524/186, 236; 564/268

[56] References Cited

U.S. PATENT DOCUMENTS

| | | | |
|---|---|---|---|
| 2,497,061 | 2/1950 | Kellog | 99/163 |
| 3,256,331 | 6/1966 | Jones et al. | 564/259 |
| 4,028,412 | 6/1977 | Gehlhaus et al. | 252/184 |
| 4,152,531 | 5/1979 | Hollingshead | 568/793 |
| 4,316,996 | 2/1982 | Collonge et al. | 568/784 |
| 4,566,901 | 1/1986 | Martin et al. | 504/112 |
| 4,576,628 | 3/1986 | Martin et al. | 504/111 |

FOREIGN PATENT DOCUMENTS

| | | |
|---|---|---|
| 1053668 | 5/1979 | Canada. |
| 0052573 | 4/1984 | European Pat. Off. |
| 299323 | 4/1990 | Japan. |

OTHER PUBLICATIONS

J. L. Brokenshire et al., J. Am. Chem. Soc., 94 7040 (1972).
G. D. Mendenhall et al., J. Am. Chem. Soc. 95 2963 (1973).
Chem. Abst. 113, 192699f (1990).
Derwent Abst. (1990) 159052/21.

*Primary Examiner*—Glennon H. Hollrah
*Assistant Examiner*—Peter G. O'Sullivan
*Attorney, Agent, or Firm*—Luther A. R. Hall

[57] ABSTRACT

Sterically hindered oximes provide polyolefin compositions, including those also containing a phenolic antioxidant, with improved resistance to discoloration during processing at elevated temperatures.

9 Claims, No Drawings

STERICALLY HINDERED OXIME COLOR IMPROVERS FOR POLYOLEFIN PROCESSING

This is a divisional of application Ser. No. 07/601,198, filed on Oct. 22, 1990, now U.S. Pat. No. 5,134,183, issued on Jul. 28, 1992.

BACKGROUND OF THE INVENTION

U.S. Pat. No. 2,497,061 describes alkanedione dioximes as antioxidants for elastomers and drying oils. No mention is made of their use as color improvers for polyolefins during processing either alone or in combination with a phenolic antioxidant. The dioximes of U.S. Pat. No. 2,497,061 are not sterically hindered and fall outside the scope of the instant invention.

The synthesis of sterically hindered oximes is described in Canadian Patent No. 1,053,668. Their use as "spin-labels in molecules of biological interest, as inhibitors of vinyl polymerization, or inhibitors of hydrocarbon oxidation ..." is suggested within the text. Their use as color improvers during polyolefin processing is not suggested. The bis(sterically hindered oximes) of the present invention are new compounds.

J. L. Brokenshire, et al., J. Amer. Chem. Soc., 94, 7040 (1972); G. D. Mendenhall, et al., J. Amer. Chem. Soc., 95, 2963 (1973); and Canadian Patent No. 1,053,668 all describe the preparation of stable iminoxy radicals from sterically hindered oximes.

European Patent Application 52,573 discloses the use of hydroxylamines plus oximes to improve the color of phenolic antioxidants during preparation of said antioxidants. Diethylhydroxylamine and methyl ethyl ketoxime are preferred components.

U.S. Pat. Nos. 4,566,901 and 4,576,628 disclose oxime ethers which are useful for agricultural purposes as safeners. U.S. Pat. No. 4,028,412 describes α-hydroxy (benzoin) oximes as chelating agents for copper. The instant sterically hindered oximes are structurally distinguished from the compounds described in these patents.

OBJECTS OF THE INVENTION

One object of the invention is to provide polyolefin compositions stabilized against discoloration during processing by the presence of an effective stabilizing amount of a sterically hindered oxime.

Another object of this invention is to provide new sterically hindered oximes useful as process stabilizers for polyolefins.

DETAILED DISCLOSURE

The instant invention pertains to a polyolefin composition stabilized against discoloration during processing which comprises (a) a polyolefin, subject to discoloration during processing, and (b) an effective stabilizing amount of a compound of the formula I

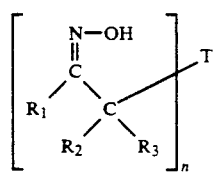

(I)

wherein $R_1$ is a tert-alkyl group of 4 to 18 carbon atoms, aryl of 6 to 10 carbon atoms or said aryl substituted by one or two alkyl of 1 to 4 carbon atoms or by one or two alkoxy of 1 to 4 carbon atoms, $R_2$ and $R_3$ are independently alkyl of 1 to 18 carbon atoms, cycloalkyl of 5 to 12 carbon atoms, phenylalkyl of 7 to 9 carbon atoms, aryl of 6 to 10 carbon atoms, or said aryl or said phenylalkyl substituted on the phenyl ring by one or two alkyl of 1 to 4 carbon atoms or by one or two alkoxy of 1 to 4 carbon atoms; or $R_2$ and $R_3$ together are a straight or branched chain alkylene of 4 to 10 carbon atoms, n is an integer from 1 to 4, when n is 1, T is alkyl of 1 to 18 carbon atoms, cycloalkyl of 5 to 12 carbon atoms, phenylalkyl of 7 to 9 carbon atoms, aryl of 6 to 10 carbon atoms, or said aryl or said phenylalkyl substituted on the phenyl ring by one or two alkyl of 1 to 4 carbon atoms or by one or two alkoxy of 1 to 4 carbon atoms, when n is 2, T is alkylene of 2 to 12 carbon atoms, xylylene, arylene of 6 to 10 carbon atoms or said arylene substituted by one or two alkyl of 1 to 4 carbon atoms or by one or two alkoxy of 1 to 4 carbon atoms, and when n is 3 or 4, T is alkanetriyl of 3 to 10 carbon atoms, or alkanetetrayl of 4 to 10 carbon atoms.

Preferably, $R_1$ is tert-alkyl of 4 to 8 carbon atoms, phenyl or phenyl substituted by one or two alkyl of 1 to 2 carbon atoms or by one or two alkoxy of 1 to 2 carbon atoms.

$R_2$ and $R_3$ are preferably independently alkyl of 1 to 8 carbon atoms.

Preferably, n is 1 or 2.

When n is 1, T is preferably alkyl of 8 to 18 carbon atoms or benzyl.

When n is 2, T is preferably alkylene of 2 to 10 carbon atoms.

Most preferably, $R_1$ is tert-butyl, phenyl or phenyl substituted by one or two methyl or by one or two methoxy.

$R_2$ and $R_3$ are most preferably methyl.

When n is 1, T is most preferably alkyl of 12 to 18 carbon atoms, especially n-octadecyl.

When n is 2, T is most preferably alkylene of 4 to 8 carbon atoms, especially hexamethylene.

When $R_1$ is tert-alkyl, it is, for example, tert-butyl, tert-amyl, tert-octyl, tert-dodecyl or tert-tridecyl. When any of $R_1$, $R_2$, $R_3$ or T is alkyl, it is, for example methyl, ethyl, isopropyl, n-butyl, sec-butyl, isobutyl, tert-butyl, tert-amyl, 2-ethylhexyl, n-octyl, tert-octyl, lauryl or n-octadecyl; when said radicals are cycloalkyl, they are, for example, cyclopentyl, cyclohexyl, cyclooctyl and cyclododecyl; when said radicals are phenylalkyl, they are, for example, benzyl, phenethyl, α-methylbenzyl and α,α-dimethylbenzyl; when said radicals are aryl or substituted aryl, they are, for example, phenyl, naphthyl, tolyl, xylyl and 3,4-dimethoxyphenyl. When $R_2$ and $R_3$ together or T is alkylene, alkylene is, for example, ethylene, tetramethylene, hexamethylene, octamethylene, 2,2-dimethyl-1,3-trimethylene, dodecamethylene or 1,2-propylene; when said radicals are arylene, they are, for example, phenylene, naphthylene or dimethylphenylene; when T is alkanetriyl or alkanetetrayl, T is, for example, glyceryl, the alkanetriyl radical derived from trimethylolethane or from trimethylolpropane, pentaerythrityl or 1,2,3,4-butanetetrayl.

The compounds of this invention are conveniently obtained by the preparation of an appropriate tertiary nitrile intermediate followed by reaction of said nitrile with a tert-alkyllithium. The desired sterically hindered oxime is isolated after treatment with ethanol, acetic acid and hydroxylamine hydrochloride following the method of Mendenhall, et al., J. Amer. Chem. Soc., 95, 2963 (1973). The intermediates required to carry out the Mendenhall process are largely items of commerce or can be made by methods known in the art.

Substrates in which the compounds of this invention are particularly useful are the polyolefins, such as polyethylene and polypropylene. Polypropylene is particularly well stabilized by the instant compounds during processing.

While the instant compounds of formula I are quite effective process stabilizers for polyolefins when used alone, compositions which also contain a phenolic antioxidant are also extremely well stabilized during processing by this combination of process stabilizers.

The compounds of formula I where n is 2 to 4 are new compounds not disclosed or suggested by the prior art. Compounds where n is 2 are particularly preferred.

In general polymers which can be stabilized include

1. Polymers of monoolefins and diolefins, for example polyethylene (which optionally can be crosslinked), polypropylene, polyisobutylene, polybutene-1, polymethylpentene-1, polyisoprene or polybutadiene, as well as polymers of cycloolefins, for instance of cyclopenteneor norbornene.

2. Mixtures of the polymers mentioned under 1), for example mixtures of polypropylene with polyisobutylene.

3. Copolymers of monoolefins and diolefins with each other or with other vinyl monomers, such as, for example, ethylene/propylene, propylene/butene-1, propylene/isobutylene, ethylene/butene-1, propylene/butadiene, isobutylene/isoprene, ethylene/alkyl acrylates, ethylene/alkyl methacrylates, ethylene/vinyl acetate or ethylene/acrylic acid copolymers and their salts (ionomers) and terpolymers of ethylene with propylene and a diene, such as hexadiene, dicyclopentadiene or ethylidene-norbornene.

4. Polystyrene, poly-(p-methylstyrene).

5. Copolymers of styrene or methylstyrene with dienes or acrylic derivatives, such as, for example, styrene/butadiene, styrene/acrylonitrile, styrene/ethyl methacrylate, styrene/butadiene/ethyl acrylate, styrene/acrylonitrile/methyl acrylate; mixtures of high impact strength from styrene copolymers and another polymer, such as, for example, from a polyacrylate, a diene polymer or an ethylene/propylene/diene terpolymer; and block polymers of styrene, such as, for example, styrene/butadiene/styrene, styrene/isoprene/styrene, styrene/ethylene/butylene/styrene or styrene/ethylene/propylene/styrene.

6. Graft copolymers of styrene, such as, for example, styrene on polybutadiene, styrene and acrylonitrile on polybutadiene, styrene and alkyl acrylates or methacrylates on polybutadiene, styrene and acrylonitrile on ethylene/propylene/diene terpolymers, styrene and acrylonitrile on polyacrylates or polymethacrylates, styrene and acrylonitrile on acrylate/butadiene copolymers, as well as mixtures thereof with the copolymers listed under 5), for instance the copolymer mixtures known as ABS-, MBS-, ASA- or AES-polymers.

7. Halogen-containing polymers, such as polychloroprene, chlorinated rubbers, chlorinated or sulfochlorinated polyethylene, epichlorohydrin homo- and copolymers, polymers from halogen-containing vinyl compounds, as for example, polyvinylchloride, polyvinylidene chloride, polyvinyl fluoride, polyvinylidene fluoride, as well as copolymers thereof, as for example, vinyl chloride/vinylidene chloride, vinyl chloride/vinyl acetate, vinylidene chloride/vinyl acetate copolymers, or vinyl fluoride/vinyl ether copolymers.

8. Polymers which are derived from $\alpha,\beta$-unsaturated acids and derivatives thereof, such as polyacrylates and polymethacrylates, polyacrylamide and polyacrylonitrile.

9. Copolymers from the monomers mentioned under 8) with each other or with other unsaturated monomers, such as, for instance, acrylonitrile/butadiene, acrylonitrile/alkyl acrylate, acrylonitrile/alkoxyalkyl acrylate or acrylonitrile/vinyl halogenide copolymers or acrylonitrile/alkyl methacrylate/butadiene terpolymers.

10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinylbutyral, polyallyl phthalate or polyallyl-melamine.

11. Homopolymers and copolymers of cyclic ethers, such as polyalkylene glycols, polyethylene oxide, polypropylene oxide or copolymers thereof with bis-glycidyl ethers.

12. Polyacetals, such as polyoxymethylene and those polyoxymethylenes which contain ethylene oxide as comonomer.

13. Polyphenylene oxides and sulfides, and mixtures of polyphenylene oxides with polystyrene.

14. Polyurethanes which are derived from polyethers, polyesters or polybutadienes with terminal hydroxyl groups on the one side and aliphatic or aromatic polyisocyanates on the other side, as well as precursors thereof (polyisocyanates, polyols or prepolymers).

15. Polyamides and copolyamides which are derived from diamines and dicarboxylic acids and/or from aminocarboxylic acids or the corresponding lactams, such as polyamide 4, polyamide 6, polyamide 6/6, polyamide 6/10, polyamide 11, polyamide 12, poly-2,4,4-trimethylhexamethylene terephthalmide, poly-p-phenylene terephthalamide or poly-m-phenylene isophthalamide, as well as copolymers thereof with polyethers, such as for instance with polyethylene glycol, polypropylene glycol or polytetramethylene glycols.

16. Polyureas, polyimides and polyamide-imides.

17. Polyesters which are derived from dicarboxylic acids and diols and/or from hydroxycarboxylic acids or the corresponding lactones, such as polyethylene terephthalate, polybutylene terephthalate, poly-1,4-dimethylol-cyclohexane terephthalate, poly-[2,2-(4-hydroxyphenyl)-propane] terephthalate and polyhydroxybenzoates as well as block-copolyether-esters derived from polyethers having hydroxyl end groups.

18. Polycarbonates.

19. Polysulfones, polyethersulfones and polyetherketones.

20. Crosslinked polymers which are derived from aldehydes on the one hand and phenols, ureas and melamines on the other hand, such as phenol/formaldehyde resins, urea/formaldehyde resins and melamine/formaldehyde resins.

21. Drying and non-drying alkyd resins.

22. Unsaturated polyester resins which are derived from copolyesters of saturated and unsaturated dicarboxylic acids with polyhydric alcohols and vinyl compounds as crosslinking agents, and also halogen-containing modifications thereof of low flammability.

23. Thermosetting acrylic resins, derived from substituted acrylic esters, such as epoxy-acrylates, urethane-acrylates or polyester acrylates.

24. Alkyd resins, polyester resins or acrylate resins in admixture with melamine resins, urea resins, polyisocyanates or epoxide resins as crosslinking agents.

25. Crosslinked epoxide resins which are derived from polyepoxides, for example from bis-glycidyl ethers or from cycloaliphatic diepoxides.

26. Natural polymers, such as cellulose, rubber, gelatin and derivatives thereof which are chemically modified in a polymer homologous manner, such as cellulose acetates, cellulose propionates and cellulose butyrates, or the cellulose ethers, such as methyl cellulose.

27. Mixtures of polymers as mentioned above, for example PP/EPDM, Polyamide 6/EPDM or ABS, PVC/EVA, PVC/ABS, PVC/MBS, PC/ABS, PBTP/ABS.

28. Naturally occurring and synthetic organic materials which ar pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, which materials may be used as plasticizers for polymers or as textile spinning oils, as well as aqueous emulsions of such materials.

29. Aqueous emulsions of natural or synthetic rubber, e.g. natural latex or latices of carboxylated styrene-/butadiene copolymers.

30. Polysiloxanes such as the soft, hydrophilic polysiloxanes described, for example, in U.S. Pat. No. 4,259,467; and the hard polyorganosiloxanes described, for example, in U.S. Pat. No. 4,355,147.

31. Polyketimines in combination with unsaturated acrylic polyacetoacetate resins or with unsaturated acrylic resins. The unsaturated acrylic resins include the urethane acrylates, polyether acrylates, vinyl or acryl copolymers with pendant unsaturated groups and the acrylated melamines. The polyketimines are prepared from polyamines and ketones in the presence of an acid catalyst.

32. Radiation curable compositions containing ethylenically unsaturated monomers or oligomers and a polyunsaturated aliphatic oligomer.

33. Epoxymelamine resins such as light-stable epoxy resins crosslinked by an epoxy functional coetherified high solids melamine resin such as LSE-4103 (Monsanto).

In general, the compounds of the present invention are employed in from about 0.01 to about 5% by weight of the stabilized composition, although this will vary with the particular substrate and application. An advantageous range is from about 0.5 to about 2%, and especially 0.1 to about 1%.

The stabilizers of the instant invention may readily be incorporated into the organic polymers by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The resulting stabilized polymer compositions of the invention may optionally also contain from about 0.01 to about 5%, preferably from about 0.025 to about 2%, and especially from about 0.1 to about 1% by weight of various conventional additives, such as the materials listed below, or mixtures thereof.

1. Antioxidants 1.1. Alkylated monophenols, for example,
2,6-di-tert-butyl-4-methylphenol
2-tert.butyl-4,6-dimethylphenol
2,6-tert-butyl-4-ethylphenol
2,6-di-tert-butyl-4-n-butylphenol
2,6-di-tert-butyl-4-i-butylphenol
2,6-di-cyclopentyl-4-methylphenol
2-($\alpha$-methylcyclohexyl)-4,6-dimethylphenol
2,6-di-octadecyl-4-methylphenol
2,4,6-tri-cyclohexylphenol
2,6-di-tert-butyl-4-methoxymethylphenol 1.2. Alkylated hydroquinones, for example,
2,6-di-tert-butyl-4-methoxyphenol
2,5-di-tert-butyl-hydroquinone
2,5-di-tert-amyl-hydroquinone
2,6-diphenyl-4-octadecyloxyphenol 1.3. Hydroxylated thiodiphenyl ethers, for example,
2,2'-thio-bis-(6-tert-butyl-4-methylphenol)
2,2'-thio-bis-(4-octylphenol)
4,4'-thio-bis-(6-tert-butyl-3-methylphenol)
4,4'-thio-bis-(6-tert-butyl-2-methylphenol)

1.4. Alkylidene-bisphenols, for example,
2,2'-methylene-bis-(6-tert-butyl-4-methylphenol)
2,2'-methylene-bis-(6-tert-butyl-4-ethylphenol)
2,2'-methylene-bis-[4-methyl-6-($\alpha$-methylcyclohexyl)-phenol]
2,2'-methylene-bis-(4-methyl-6-cyclohexylphenol)
2,2'-methylene-bis-(6-nonyl-4-methylphenol)
2,2'-methylene-bis-[6-($\alpha$-methylbenzyl)-4-nonylphenol]
2,2'-methylene-bis-[6-($\alpha,\alpha$-dimethylbenzyl)-4-nonylphenol]
2,2'-methylene-bis-(4,6-di-tert-butylphenol)
2,2'-ethylidene-bis-(4,6-di-tert-butylphenol)
2,2'-ethylidene-bis-(6-tert-butyl-4-isobutylphenol)
4,4'-methylene-bis-(2,6-di-tert-butylphenol)
4,4'-methylene-bis-(6-tert-butyl-2-methylphenol)
1,1-bis-(5-tert-butyl-4-hydroxy-2-methylphenyl)-butane
2,6-di-(3-tert-butyl-5-methyl-2-hydroxybenzyl)-4-methylphenol
1,1,3-tris-(5-tert-butyl-4-hydroxy-2-methylphenyl)-butane
1,1-bis-(5-tert-butyl-4-hydroxy-2-methylphenyl)-3-n-dodecylmercaptobutane
ethyleneglycol bis-[3,3-bis-(3'-tert-butyl-4'-hydroxyphenyl)-butyrate]
di-(3-tert-butyl-4-hydroxy-5-methylphenyl)-dicyclopentadiene
di-[2-(3'-tert-butyl-2'-hydroxy-5'-methyl-benzyl)-6-tert-butyl-4-methylphenyl] terephthalate.

1.5. Benzyl compounds, for example,
1,3,5-tri-(3,5-di-tert-butyl-4-hydroxybenzyl)-2,4,6-trimethylbenzene
di-(3,5-di-tert-butyl-4-hydroxybenzyl) sulfide
3,5-di-tert-butyl-4-hydroxybenzyl-mercapto-acetic acid isooctyl ester
bis-(4-tert-butyl-3-hydroxy-2,6-dimethylbenzyl)dithiol terephthalate
1,3,5-tris-(3,5-di-tert-butyl-4-hydroxybenzyl) isocyanurate 1,3,5-tris-(4-tert-butyl-3-hydroxy-2,6-dimethylbenzyl) isocyanurate
3,5-di-tert-butyl-4-hydroxybenzyl-phosphoric acid dioctadecyl ester
3,5-di-tert-butyl-4-hydroxybenzyl-phosphoric acid monoethyl ester, calcium-salt 1.6. Acylaminophenols, for example,
4-hydroxy-lauric acid anilide
4-hydroxy-stearic acid anilide
2,4-bis-octylmercapto-6-(3,5-tert-butyl-4-hydroxyanilino)-s-triazine
octyl-N-(3,5-di-tert-butyl-4-hydroxyphenyl)-carbamate 1.7. Ester of β-(3,5-di-tert-butyl-4-hydroxyphenyl)-propionic acid with monohydric or polyhydric alcohols, for example,

| methanol | diethylene glycol |
| octadecanol | triethylene glycol |
| 1,6-hexanediol | pentaerythritol |
| neopentyl glycol | tris-hydroxyethyl isocyanurate |
| thiodiethylene glycol | di-hydroxyethyl oxalic acid diamide |

1.8. Esters of β-(5-tert-butyl-4-hydroxy-3-methylphenyl)-propionic acid with monohydric or polyhydric alcohols, for example,

| methanol | diethylene glycol |
| octadecanol | triethylene glycol |
| 1,6-hexanediol | pentaerythritol |
| neopentyl glycol | tris-hydroxyethyl isocyanurate |
| thiodiethylene glycol | di-hydroxyethyl oxalic acid diamide |

1.9. Amides of β-(3,5-di-tert-butyl-4-hydroxyphenyl)-propionic acid for example,
N,N'-di-(3,5-di-tert-butyl-4-hydroxyphenylpropionyl)-hexamethylenediamine
N,N'-di-(3,5-di-tert-butyl-4-hydroxyphenylpropionyl)-trimethylenediamine
N,N'-di-(3,5-di-tert-butyl-4-hydroxyphenylpropionyl)-hydrazine 1.10 Diarylamines, for example, diphenylamine, N-phenyl-1-naphthylamine, N-(4-tert-octylphenyl)-1-naphthylamine, 4,4'-di-tert-octyl-diphenylamine, reaction product of N-phenylbenzylamine and 2,4,4-trimethylpentene, reaction product of diphenylamine and 2,4,4-trimethylpentene, reaction product of N-phenyl-1-naphthylamine and 2,4,4-trimethylpentene.

2. UV absorbers and light stabilizers 2.1. 2-(2'-Hydroxyphenyl)-benzotriazoles, for example, the 5'-methyl-, 3',5'-di-tert-butyl-, 5'-tert-butyl-, 5'-(1,1,3,3-tetramethylbutyl)-, 5-chloro-3',5'-di-tert-butyl-, 5-chloro-3'-tert-butyl-5'-methyl-, 3'-sec-butyl-5'-tert-butyl-, 4'-octoxy, 3',5'-di-tert-amyl-, 3',5'-bis-(α,α-dimethylbenzyl), 3'-tert-butyl-5'-(2-(omega-hydroxy-octa-(ethyleneoxy)carbonyl-ethyl)-, 3'-dodecyl-5'-methyl-, and 3'-tert-butyl-5'-(2-octyloxycarbonyl)ethyl-, and dodecylated-5'-methyl derivatives.

2.2. 2-Hydroxy-benzophenones, for example, the 4-hydroxy-, 4-methoxy-, 4-octoxy, 4-decyloxy-, 4-dodecyloxy-, 4-benzyloxy, 4,2',4'-trihydroxy- and 2'-hydroxy-4,4'-dimethoxy derivatives.

2.3. Esters of optionally substituted benzoic acids for example, phenyl salicylate, 4-tert-butylphenyl salicylate, octylphenyl salicylate, dibenzoylresorcinol, bis-(4-tert-butylbenzoyl)-resorcinol, benzoylresorcinol, 3,5-di-tert-butyl-4-hydroxybenzoic acid 2,4-di-tert-butylphenyl ester and 3,5-di-tert-butyl-4-hydroxybenzoic acid hexadecyl ester.

2.4. Acrylates, for example, α-cyano-β,β-diphenylacrylic acid ethyl ester or isooctyl ester, α-carbomethoxy-cinnamic acid methyl ester, α-cyano-β-methyl-p-methoxy-cinnamic acid methyl ester or butyl ester, α-carbomethoxy-p-methoxy-cinnamic acid methyl ester, N-(β-carbomethoxy-β-cyanovinyl)-2-methyl-indoline.

2.5. Nickel compounds, for example, nickel complexes of 2,2'-thio-bis-[4-(1,1,3,3-tetramethylbutyl)-phenol], such as the 1:1 or 1:2 complex, optionally with additional ligands such as n-butylamine, triethanolamine or N-cyclohexyl-diethanolamine, nickel dibutyl-dithiocarbamate, nickel salts of 4-hydroxy-3,5-di-tert-butylbenzylphosphonic acid monoalkyl esters, such as of the methyl, ethyl or butyl ester, nickel complexes of ketoximes such as of 2-hydroxy-4-methyl-phenyl undecyl ketoxime, nickel complexes of 1-phenyl-4-lauroyl-5-hydroxy-pyrazole, optionally with additional ligands.

2.6. Sterically hindered amines, for example bis-(2,2,6,6-tetramethylpiperidyl) sebacate, bis-(1,2,2,6,6-pentamethylpiperidyl) sebacate, n-butyl-3,5-di-tert.butyl-4-hydroxybenzyl malonic acid bis-(1,2,2,6,6-pentanemethylpiperidyl)ester, condensation product of 1-hydroxyethyl-2,2,6,6-tetramethyl-4-hydroxypiperidine and succinic acid, condensation product of N,N'-(2,2,6,6-tetramethylpiperidyl)-hexamethylenediamine and 4-tert-octylamino-2,6-dichloro-s-triazine, tris-(2,2,6,6-tetramethylpiperidyl)-nitrilotriacetate, tetrakis-(2,2,6,6-tetramethyl-4-piperidyl) 1,2,3,4-butanetetracarboxylate, 1,1'(1,2-ethanediyl)-bis-(3,3,5,5-tetramethyl-piperazinone).

2.7. Oxalic acid diamides, for example, 4,4'-di-octyloxy-oxanilide, 2,2'-di-octyloxy-oxanilide, 2,2'-di-octyloxy-5,5'-di-tert-butyl-oxanilide, 2,2'-di-dodecyloxy-5,5'-di-tert-butyl-oxanilide, 2-ethoxy-2'-ethyl-oxanilide, N,N'-bis (3-dimethylaminopropyl)-oxalamide, 2-ethoxy-5-tert-butyl-2'-ethyloxanilide and its mixture with 2-ethoxy-2'-ethyl-5,4'-di-tert-butyloxanilide and mixtures of ortho- and para-methoxy- as well as of o- and p-ethoxy-disubstituted oxanilides.

2.8. Hydroxyphenyl-s-triazines, for example 2,6-bis-(2,4-dimethylphenyl)-4-(2-hydroxy-4-octyloxyphenyl)-s-triazine; 2,6-bis-(2,4-dimethylphenyl)-4-(2,4-dihydroxyphenyl)-s-triazine; 2,4-bis(2,4-dihydroxyphenyl)-6-(4-chlorophenyl)-s-triazine; 2,4-bis[2-hydroxy-4-(2-hydroxyethoxy)phenyl]-6-(4-chlorophenyl)-s-triazine; 2,4-bis[2-hydroxy-4-(2-hydroxy-4-(2-hydroxyethoxy)-phenyl]-6-(2,4-dimethylphenyl)-s-triazine; 2,4-bis[2-hydroxy-4-(2-hydroxyethoxy)phenyl]-6-(4-bromophenyl)-s-triazine; 2,4-bis[2-hydroxy-4-(2-acetoxyethoxy)phenyl]-6-(4-chlorophenyl)-s-triazine, 2,4-bis(2,4-dihydroxyphenyl)-6-(2,4-dimethylphenyl)-s-triazine.

3. Metal deactivators, for example, N,N'-diphenyloxalic acid diamide, N-salicylal-N'-salicyloylhydrazine, N,N'-bis-salicyloylhydrazine, N,N'-bis-(3,5-di-tert-butyl-4-hydroxyphenylpropionyl)hydrazine, 3-salicyloylamino-1,2,4-triazole, bis-benzylidene-oxalic acid dihydrazide.

4. Phosphites and phosphonites, for example, triphenyl phosphite, diphenylalkyl phosphites, phenyldialkyl phosphites, tri-(nonylphenyl) phosphite, trilauryl phosphite, trioctadecyl phosphite, di-stearyl-pentaerythritol diphosphite, tris-(2,4-di-tert-butylphenyl) phosphite, di-isodecylpentaerythritol diphosphite, di-(2,4-di-tert-butylphenyl)pentaerythritol diphosphite, tristearylsorbitol triphosphite, tetrakis-(2,4-di-tert-butylphenyl) 4,4'-diphenylylenediphosphonite.

5. Compounds which destroy peroxide, for example, esters of β-thiodipropionic acid, for example the lauryl, stearyl, myristyl or tridecyl esters, mercapto-benzimidazole or the zinc salt of 2-mercaptobenzimidazole, zinc dibutyl-dithiocarbamate, dioctadecyl disulfide, pentaerythritol tetrakis-(β-dodecylmercapto)-propionate.

6. Hydroxylamines, for example, N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

7. Nitrones, for example, N-benzyl-alpha-phenyl nitrone, N-ethyl-alpha-methyl nitrone, N-octyl-alpha-heptyl nitrone, N-lauryl-alpha-undecyl nitrone, N-tetradecyl-alpha-tridecyl nitrone, N-hexadecyl-alpha-pentadecyl nitrone, N-octadecyl-alpha-heptadecylnitrone, N-hexadecyl-alpha-heptadecyl nitrone, N-octadecyl-alpha-pentadecyl nitrone, N-heptadecyl-alpha-heptadecyl nitrone, N-octadecyl-alpha-hexadecyl nitrone, nitrone derived from N,N-dialkylhydroxylamine derived from hydrogenated tallow amine.

8. Polyamide stabilizers, for example copper salts in combination with iodides and/or phosphorus compounds and salts of divalent manganese.

9. Basic co-stabilizers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example Ca stearate, Zn stearate, Mg stearate, Na ricinoleate and K palmitate, antimony pyrocatecholate or zinc pyrocatecholate.

10. Nucleating agents, for example, 4-tert-butyl-benzoic acid, adipic acid, diphenylacetic acid.

11. Fillers and reinforcing agents, for example, calcium carbonate, silicates, glass fibers, asbestos, talc, kaolin, mica, barium sulfate, metal oxides and hydroxides, carbon black, graphite.

12. Other additives, for example, plasticizers, lubricants, emulsifiers, pigments, optical brighteners, flame-proofing agents, anti-static agents, blowing agents and thiosynergists such as dilauryl thiodipropionate or distearyl thiodipropionate.

The phenolic antioxidant of particular interest is selected from the group consisting of n-octadecyl 3,5-di-tert-butyl-4-hydroxyhydrocinnamate, neopentanetetrayl tetrakis(3,5-di-tert-butyl-4-hydroxyhydrocinnamate), di-n-octadecyl 3,5-di-tert-butyl-4-hydroxybenzylphosphonate, 1,3,5-tris(3,5-di-tert-butyl-4-hydroxybenzyl)isocyanurate, thiodiethylene bis(3,5-di-tert-butyl-4-hydroxyhydrocinnamate), 1,3,5-trimethyl-2,4,6-tris(3,5-di-tert-butyl-4-hydroxybenzyl)benzene, 3,6-dioxaoctamethylene bis(3-methyl-5-tert-butyl-4-hydroxyhydrocinnamate), 2,6-di-tert-butyl-p-cresol, 2,2'-ethylidene-bis(4,6-di-tert-butylphenol), 1,3,5-tris(2,6-dimethyl-4-tert-butyl-3-hydroxybenzyl)isocynurate, 1,1,3,-tris(2-methyl-4-hydroxy-5-tert-butylphenyl)butane, 1,3,5-tris[2-(3,5-di-tert-butyl-4-hydroxyhydrocinnamoyloxy)ethyl]isocyanurate, 3,5-di-(3,5-di-tert-butyl-4-hydroxybenzyl)mesitol, hexamethylene bis(3,5-di-tert-butyl-4-hydroxyhydrocinnamate), 1-(3,5-di-tert-butyl-4-hydroxyanilino)-3,5-di(octylthio)-s-triazine, N,N'-hexamethylene-bis(3,5-di-tert-butyl-4-hydroxyhydrocinnamamide), calcium bis(ethyl 3,5-di-tert-butyl-4-hydroxybenzylphosphonate), ethylene bis[3,3-di(3-tert-butyl-4-hydroxyphenyl)butyrate], octyl 3,5-di-tert-butyl-4-hydroxybenzylmercaptoacetate, bis(3,5-di-tert-butyl-4-hydroxyhydrocinnamoyl)hydrazide, and N,N'-bis[2-(3,5-di-tert-butyl-4-hydroxyhydrocinnamoyloxy)-ethyl]-oxamide.

A most preferred phenolic antioxidant is neopentanetetrayl tetrakis(3,5-di-tert-butyl-4-hydroxyhydrocinnamate), n-octadecyl 3,5-di-tert-butyl-4-hydroxyhydrocinnamate, 1,3,5-trimethyl-2,4,6-tris(3,5-di-tert-butyl-4-hydroxybenzyl)benzene, 1,3,5-tris(3,5-di-tert-butyl-4-hydroxybenzyl)isocyanurate, 2,6-di-tert-butyl-p-cresol or 2,2'-ethylidene-bis(4,6-di-tert-butylphenol).

The hindered amine compound of particular interest is selected from the group consisting of bis(2,2,6,6-tetramethylpiperidin-4-yl) sebacate, bis(1,2,2,6,6-pentamethylpiperidin-4-yl) sebacate, di(1,2,2,6,6-pentamethylpiperidin-4-yl) (3,5-di-tert-butyl-4-hydroxybenzyl)butylmalonate, 4-benzoyl-2,2,6,6-tetramethylpiperidine, 4-stearyloxy-2,2,6,6-tetramethylpiperidine, 3-n-octyl-7,7,9,9-tetramethyl-1,3,8-triaza-spiro[4.5]decane-2,4-dione, tris(2,2,6,6-tetramethylpiperidin-4-yl) nitrilotriacetate, 1,2-bis(2,2,6,6-tetramethyl-3-oxopiperazin-4-yl)ethane, 2,2,4,4-tetramethyl-7-oxa-3,20-diaza-21-oxodispiro[5.1.11.2] heneicosane, polycondensation product of 2,4-dichloro-6-tert-octylamino-s-triazine and 4,4'-hexamethylenebis(amino-2,2,6,6-tetramethylpiperidine), polycondensation product of 1-(2-hydroxyethyl)-2,2,6,6-tetramethyl-4-hydroxypiperidine and succinic acid, polycondensation product of 4,4'-hexamethylene-bis-(amino-2,2,6,6-tetramethylpiperidine) and 1,2-dibromoethane, tetrakis(2,2,6,6-tetramethylpiperidin-4-yl) 1,2,3,4-butanetetracarboxylate, tetrakis(1,2,2,6,6-pentamethylpiperidin-4-yl) 1,2,3,4-butanetetracarboxylate, polycondensation product of 2,4-dichloro-6-morpholino-s-triazine and 4,4'-hexamethylenebis(amino-2,2,6,6-tetramethylpiperidine), N,N',N'',N'''-tetrakis[(4,6-bis(butyl-2,2,6,6-tetramethyl-piperidin-4-yl)-amino-s-triazin-2-yl]-1,10-diamino-4,7-diazadecane, mixed [2,2,6,6-tetramethylpiperidin-4yl/β,β,β',β'-tetramethyl-3,9-(2,4,8,10-tetraoxaspiro[5.5]-undecane) diethyl]1,2,3,4-butanetetracarboxylate, mixed [1,2,2,6,6-pentamethylpiperidin-4-yl/β,β,β',β'-tetramethyl-3,9-(2,4,8,10-tetraoxaspiro[5.5]-undecane)diethyl]1,2,3,4-butanetetracarboxylate, octamethylene bis(2,2,6,6-tetramethylpiperidin-4-carboxylate) and 4,4'-ethylenebis(2,2,6,6-tetramethylpiperazin-3-one).

A most preferred hindered amine compound is bis(2,2,6,6-tetramethylpiperidin-4-yl) sebacate, the polycondensation product of 1-(2-hydroxyethyl)-2,2,6,6-tetramethyl-4-hydroxypiperdine and succinic acid, the polycondensation product of 2,4-dichloro-6-tert-octylamino-s-triazine and 4,4'-hexamethylenebis-(amino-2,2,6,6-tetramethylpiperidine) or N,N',N'',N'''-tetrakis[(4,6-bis(butyl-(2,2,6,6-tetramethyl-piperidin-4-yl)amino)-s-triazine-2-yl]1,10-diamino-4,7-diazadecane.

The following examples are presented for the purpose of illustration only and are not to be construed to limit the nature of scope of the instant invention in any manner whatsoever.

EXAMPLE 1

Di-tert-butyl Ketoxime

The title compound is prepared according to the procedure of G. D. Mendenhall and K. U. Ingold, J. Amer. Chem. Soc., 95, 2963 (1973).

EXAMPLE 2

2-Cyano-2-methyleicosane

To a solution of 24 mL of a 2.5M n-butyllithium solution in hexanes and 60 mL of tetrahydrofuran at −78° C. is added dropwise 6.07 g of diisopropylamine. After the reaction mixture is stirred at this temperature for 15 minutes, a solution of 5.5 mL of isobutyronitrile in 60 mL of tetrahydrofuran is added dropwise and the resultant reaction mixture is stirred for 2 hours at −78° C. To the reaction mixture at room temperature is added a solution of 20 g of 1-bromooctadecane in 50 mL of tetrahydrofuran. The reaction mixture is stirred for 18 hours at room temperature and then 100 mL of saturated ammonium chloride is added. To the reaction mixture is added 100 mL of diethyl ether and the organic phase is separated. The organic phase is dried over anhydrous magnesium sulfate and the solvent is removed in vacuo to give 18.2 g of the title compound as a white solid. The $^1$H NMR spectrum is consistent with the desired product.

EXAMPLE 3

Tert-butyl 2-Methyleicosan-2-yl Ketooxime

To a suspension of 2-cyano-2-methyleicosane in 30 mL of pentane cooled with a water bath is added dropwise 17.6 mL of a 1.7M tert-butyllithium solution in pentane. The reaction mixture is heated at reflux for 1 hours. To the reaction mixture is added sequentially 3 mL of ethanol, 2 mL of acetic acid, and 2.12 g of hydroxylamine hydrochloride and the resultant reaction mixture is stirred for 18 hours at room temperature. The precipitate is removed by filtration and the collected solids are recrystallized from hexane to give 6.1 g (51.4%) of the title compound as a white solid melting at 92°–94° C.

Analysis: Calcd. for $C_{26}H_{53}NO$: C, 78.9; H, 13.5; N, 3.5. Found: C, 79.2; H, 13.7; N, 3.4.

EXAMPLE 4

2,9-Dicyano-2,9-dimethyldecane

By the procedure used to prepare the compound of Example 2, the title compound is prepared from 24 mL of a 2.5M n-butyllithium solution in hexanes, 6.07 g of diisopropylamine, 5.5 mL of isobutyronitrile, 7.32 g of 1,6-dibromohexane, and 120 mL of tetrahydrofuran. The IR and $^1$H NMR spectra of the white solid (7.7 g) obtained were consistent with structure of the desired product.

EXAMPLE 5

2,2,4,4,11,11,13,13-Octamethyl-3,12-dioximinotetradecane

By the procedure used to prepare the compound of Example 3, the title compound is prepared from 7.7 g of 2,9-dicyano-2,9-dimethyldecane, 35.3 mL of a 1.7M tert-butyllithium solution in pentane, 30 mL of pentane, 6 mL of ethanol, 4 mL of acetic acid, and 4.24 g of hydroxylamine hydrochloride. The residue is purified by trituration sequentially with methanol and hot ethanol to give 4.9 g (44%) of the title compound as a white solid melting at 203°–209° C.

Analysis: Calcd. for $C_{22}H_{44}N_2O_2$: C, 71.7; H, 12.0; N, 7.6. Found: C, 71.8; H, 11.8; N, 7.4.

EXAMPLE 6

Tert-butyl 3,4-Dimethoxyphenyl Ketooxime

By the procedure used to prepare the compound of Example 3, the title compound is prepared from 10.0 g of 3,4-dimethoxybenzonitrile, 36 mL of a 1.7M tert-butyllithium solution in pentane, 30 mL of pentane, 6 mL of ethanol, 4 mL of acetic acid, and 4.24 g of hydroxylamine hydrochloride. The residue is purified by recrystallization from methanol to give 2.1 g (15%) of the title compound as a white solid melting at 203°–209° C.

Analysis: Calcd. for $C_{13}H_{19}NO$: C, 65.8; H, 8.1; N, 5.9. Found: C, 65.7; H, 8.2; N, 5.9.

EXAMPLE 7

Process Stabilization of Polypropylene at 536° F. (280° C.)

This example illustrates the thermal stabilizing effectiveness of the instant compounds in new technology polypropylene.

The base formulation comprises unstabilized new technology polypropylene (PROFAX 6501, HIMONT) containing 0.1% by weight of calcium stearate. The test stabilizer is dry blended, if a solid, or solvent blended, if a liquid, onto polypropylene from a solution in methylene chloride. After removal of the solvent by evaporation under reduced pressure, the stabilized resin formulation is extruded at 80 rpm from a 1 inch (2.54 cm) diameter extruded at 536° F. (280° C.). The residence time in the extruder is 45 seconds.

After each of the first and fifth extrusions, the melt flow rate (in grams/10 minutes) is measured according to ASTM method D-1238 on the pellets obtained. The closer the melt flow rate after the fifth extrusion is to the melt flow rate after the first extrusion the less polymer degradation has occurred. Close values would indicate superior process stabilization efficacy bestowed by the test stabilizer.

The test results are shown in the table below.

| Additive* | Additive Concentration (% by weight) | Melt Flow Rate After Extrusion | |
|---|---|---|---|
| | | 1 | 5 |
| None | — | 10.7 | 30 |
| AO A | 0.1 | 4.3 | 12.7 |
| Example 1 | 0.1 | 3.5 | 15.6 |
| Example 3 | 0.1 | 4.1 | 18.1 |
| Example 5 | 0.1 | 3.2 | 17.2 |

*AO A is neopentanetetrayl tetrakis(3,5-di-tert-butyl-4-hydroxyhydrocinnamate).

These data show that the sterically hindered oximes provide improved melt flow values compared to the control. After one extrusion the melt flow values are similar to that provided by a phenolic antioxidant.

EXAMPLE 8

Color Stabilization of Polypropylene Processed at 536° F. (280° C.)C

When polypropylene is extruded as described in Example 7, resin pellets obtained after the first and fifth extrusions are compression molded into 125 mil (3.2 mm) thick plaques at 380° F. (193° C.) and specimen yellowness index (YI) values are determined according to ASTM method D-1925. Low YI values indicate less yellowing and discoloration.

The results are given in the table below.

| Additive* | Additive Concentration (% by weight) | Yellowness Index Value After Extrusion | |
|---|---|---|---|
| | | 1 | 5 |
| None | — | 2.2 | 3.3 |
| AO A | 0.1 | 8.4 | 10.5 |
| Example 1 | 0.1 | 0.2 | 3.4 |
| Example 3 | 0.1 | 0.6 | 3.2 |
| Example 5 | 0.1 | 0.5 | 5.7 |

*AO A is neopentanetetrayl tetrakis(3,5-di-tert-butyl-4-hydroxyhydrocinnamate).

Improved resistance to discoloration as measured by yellowness index values is observed when the instant sterically hindered oximes are used compared to conventional hindered phenolic antioxidants. Surprisingly, the YI color after one extrusion is superior to that of the base resin itself when the hindered oximes are employed.

EXAMPLE 9

Process Stabilization of Polypropylene at 536° F. (280° C.)

Following the procedure set forth in Example 7, a combination of instant sterically hindered oxime plus a phenolic antioxidant are used to stabilize the polypropylene. The melt flow rates after the first and fifth extrusions are measured to assess the effectiveness of this combination of stabilizers.

The test results are shown in the table below.

| Additive* | Additive Concentration (% by weight) | Melt Flow Rate After Extrusion | |
|---|---|---|---|
| | | 1 | 5 |
| None | — | 10.7 | 30 |
| AO A | 0.1 | 4.3 | 12.7 |
| AO A plus Example 1 | 0.1 0.05 | 3.5 | 12.1 |
| AO A plus Example 3 | 0.1 0.05 | 4.4 | 14.8 |
| AO A plus Example 5 | 0.1 0.05 | 4.0 | 18.1 |

*AO A is neopentanetetrayl tetrakis(3,5-ditert-butyl-4-hydroxyhydrocinnamate).

These data show that the sterically hindered oximes in combination with hindered phenolic antioxidants provide improved melt flow values compared to the control.

EXAMPLE 10

Color Stabilization of Polypropylene Processed at 536° F. (280° C.)

Following the procedure set forth in Example 7, a combination of instant sterically hindered oxime plus a phenolic antioxidant are used to stabilize the polypropylene. The resin pellets obtained after the first and fifth extrusions are compression molded into 125 mil (3.2 mm) thick plaques at 380° F. (193° C.) and specimen yellowness index (YI) values are determined according to ASTM method D-1925. Low YI values indicate less yellowing and discoloration.

The results are given in the table below.

| Additive* | Additive Concentration (% by weight) | Yellowness Index Value After Extrusion | |
|---|---|---|---|
| | | 1 | 5 |
| None | — | 2.2 | 3.3 |
| AO A | 0.1 | 8.4 | 10.5 |
| AO A plus Example 1 | 0.1 0.05 | 5.2 | 8.0 |
| AO A plus Example 3 | 0.1 0.05 | 7.4 | 7.6 |
| AO A plus Example 5 | 0.1 0.05 | 5.0 | 7.6 |

*AO A is neopentanetetrayl tetrakis(3,5-di-tert-butyl-4-hydroxyhydrocinnamate).

Improved resistance to discoloration as measured by yellowness index values is observed when the instant sterically hindered oximes are used in combination with a conventional hindered phenolic antioxidant. The combination of phenolic antioxidant plus sterically hindered oxime provides better resistance to discoloration than use of the phenolic antioxidant alone.

What is claimed is:

1. A compound of formula I

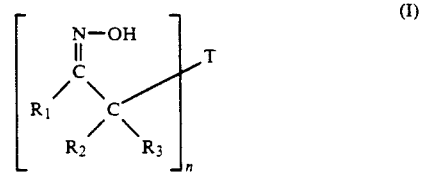

wherein $R_1$ is a tert-alkyl group of 4 to 18 carbon atoms, $R_2$ and $R_3$ are independently alkyl of 1 to 18 carbon atoms, n is 2, and T is alkylene of 2 to 12 carbon atoms.

2. A compound according to claim 1 wherein $R_1$ is tert-alkyl of 4 to 8 carbon atoms.

3. A compound according to claim 2 wherein $R_1$ is tert-butyl.

4. A compound according to claim 1 wherein $R_2$ and $R_3$ are independently alkyl of 1 to 8 carbon atoms.

5. A compound according to claim 4 wherein $R_2$ and $R_3$ are methyl.

6. A compound according to claim 1 wherein T is alkylene of 2 to 10 carbon atoms.

7. A compound according to claim 6 wherein T is alkylene of 4 to 8 carbon atoms.

8. A compound according to claim 7 wherein T is hexamethylene.

9. The compound according to claim 1 which is 2,2,4,4,11,11,13,13-octamethyl-3,12-dioximinotetradecane.

* * * * *